(12) United States Patent
Astin

(10) Patent No.: US 6,849,041 B2
(45) Date of Patent: Feb. 1, 2005

(54) PHALLUS RETENTION HARNESS (76) Inventor: Cole T. Astin, 8721 Santa Monica Blvd., #330, Los Angeles, CA (US) 90069

(*) Notice: Subject to any disclaimer, the term of this patent is extended or adjusted under 35 U.S.C. 154(b) by 0 days.

(21) Appl. No.: 10/485,421
(22) PCT Filed: Jul. 31, 2002
(86) PCT No.: PCT/US02/24509
§ 371 (c)(1),
(2), (4) Date: Jan. 30, 2004
(87) PCT Pub. No.: WO03/011061
PCT Pub. Date: Feb. 13, 2003

(65) Prior Publication Data
US 2004/0199046 A1 Oct. 7, 2004

Related U.S. Application Data
(60) Provisional application No. 60/309,035, filed on Jul. 31, 2001.

(51) Int. Cl.[7] .................................................. A61F 5/00
(52) U.S. Cl. ........................................................ 600/38
(58) Field of Search ...................................... 600/38–41

(56) References Cited

U.S. PATENT DOCUMENTS

| | | |
|---|---|---|
| 745,264 A | 11/1903 | Todd |
| 2,264,934 A | 12/1941 | Cronk |
| 4,488,541 A | 12/1984 | Garcia |
| 4,660,551 A | 4/1987 | Nishimura |
| 5,103,810 A | 4/1992 | Chang |
| D401,341 S | 11/1998 | Poubouridis |
| D410,742 S | 6/1999 | Coolidge |

Primary Examiner—John P. Lacyk
(74) Attorney, Agent, or Firm—O'Connell Law Firm (57) ABSTRACT A phallus retention harness for retaining a phallus with a base portion and an elongate body portion relative to a wearer with a pocket member for receiving and retaining the phallus wherein the pocket member has a first panel and a second panel with an inner volume between the front panel and the rear panel, an aperture in the front panel of the pocket member for enabling the elongate body portion of the phallus to extend therethrough, and an arrangement for retaining the pocket member relative to the wearer's body.

23 Claims, 11 Drawing Sheets

PHALLUS RETENTION HARNESS

TECHNICAL FIELD

The present invention relates generally to harnesses. Stated more particularly, disclosed and protected by the present patent is a harness for retaining a prosthetic phallus relative to a wearer's body.

FIELD OF THE INVENTION

One knowledgeable in the present field of endeavor will be well aware that the prior art has disclosed numerous structures and articles of apparel that act as a harness for retaining or supporting a phallus relative to a wearer's body. Some harnesses are designed for retaining a prosthetic phallus adjacent to the wearer's crotch in simulation of an erect or semi-erect male member. These harnesses, with their retained phalluses, can be worn by women for enabling them to have the sensation of having a male member and for enabling them to perform sexual acts. Some such harnesses also can be worn by men who have erectile dysfunction, want to possess a larger phallus, or simply want to wear a prosthetic phallus.

Unfortunately, harnesses of the prior art suffer from a number of limitations and disadvantages. By way of example, a review of commercially available harness will make clear that they are typically formed with a rigid crotch plate that is retained relative to a wearer by a similarly rigid belt. As a result, such prior art harnesses can be uncomfortable and restrictive to the wearer. Those harnesses can be uncomfortable for the further reason that the retained phallus, which normally must be particularly designed for each harness, has a proximal end that directly contacts the wearer's body.

In light of the foregoing and further shortcomings of the prior art, it becomes clear that there is a need in the art for a harness for retaining a phallus that is comfortable to the wearer and that achieves a number of advantages over the prior art.

SUMMARY OF THE INVENTION

Advantageously, the present invention is founded on the basic object of providing a phallus retention harness that overcomes the disadvantages exhibited by the prior art while providing a number of heretofore unrealized advantages thereover.

More particularly, a primary object of the invention is to provide a phallus retention harness that enables a phallus to be retained relative to a user in a comfortable yet effective manner.

A further object of the invention is to provide a phallus retention harness that enables a phallus to be retained relative to a wearer in an inconspicuous manner under a wearer's clothing if so desired.

Yet another object of the invention is to provide a phallus retention harness that enables phallus to be removed and replaced relative to the phallus retention harness in a simple and convenient manner.

An even further object of particular embodiments of the invention is to provide a phallus retention harness that enables a second phallus to be retained in an inwardly facing manner relative to a wearers body.

Still another object of certain embodiments of the invention is to provide a phallus retention harness that can retain a phallus relative to a wearer's hand or about a wearers body part.

These and still further objects and advantages of the invention will be obvious not only to one who has reviewed the present specification and drawings but also to one who has an opportunity to observe an embodiment of the present invention in operation.

In carrying forth these objects, one embodiment of the invention essentially comprises a phallus retention harness for retaining a phallus relative to a wearer. The phallus retention harness has a pocket member for receiving and retaining the phallus and an aperture in a front panel of the pocket member for enabling an elongate body portion of the phallus to extend therethrough. Under this arrangement, the phallus can be retained by the phallus retention harness with a base portion of the phallus disposed within an inner volume of the pocket member and the elongate body portion of the phallus projecting through the aperture.

A means for retaining the pocket member relative to the wearers body can take a variety of forms. For example, it could be a belt with a front portion and a rear portion for being disposed about a wearer's waist. In such embodiments, an upper portion of the pocket member can be coupled to the front portion of the belt and a means, such as leg straps or a cinching strap, can be provided for retaining a lower portion of the pocket member adjacent to the wearers crotch. A pocket can be provided adjacent to a rear portion of the belt for retaining articles, such as condoms or the like. The means for retaining the pocket member alternatively could comprise an underwear brief member. Furthermore, in certain embodiments, the means for retaining the pocket member could comprise a glove body portion or a strap body portion.

A hold down strap and possibly a second hold down strap can be fixed to a first or front panel of the pocket member for restraining the elongate body portion of the phallus. When the phallus is so restrained, the phallus retention harness and the phallus can be worn generally inconspicuously below a wearer's clothing if so desired.

In certain embodiments, a secondary aperture can be included in the second panel of the pocket member. When provided, the secondary aperture can enable a second phallus to be retained by the phallus retention harness with a body portion extending from the pocket member toward or into the body of the wearer. In some cases, a flat ring of resilient material can be fixed about a periphery of the secondary aperture, and a ring can be included for being associated with the aperture.

Where a belt is provided, certain embodiments of the harness can incorporate a means for adjusting the circumference of the belt. That means could take the form of hook or loop material disposed on an outside surface of the belt, an adjustment tab coupled to the belt, and loop or hook material disposed on an inside surface of the adjustment tab for engaging the hook or loop material disposed on the belt.

In any case, the first and second panels will preferably be formed from flexible material, ideally resiliently stretchable material. Also, the aperture preferably will be resiliently expandable to accommodate phalluses of varying diameters and configurations. In a most preferred embodiment, the first panel will be formed from two layers of resiliently stretchable material of a given thickness to form an outside surface of the first panel and two layers of resiliently stretchable material of a thicker thickness to form an inside surface of the first panel. The second panel can be formed of two layers of resiliently stretchable material.

A means for enabling an insertion of the phallus into the inner volume of the pocket member to allow the elongate body portion of the phallus to be inserted through the aperture from within the inner volume can simply comprise an open end of the pocket member. Alternatively, it can comprise a flap disposed in the second panel generally opposite to the aperture. The flap can be formed by first and second flap panels that overlap to create the flap whereby ready access to the aperture can be provided by a peeling back of the first and second flap panels. A hook and loop combination can be disposed on the first and second panels for retaining the first and second panels in a closed configuration.

One will appreciate that the foregoing discussion broadly outlines certain more important features of the invention to enable a better understanding of the detailed description that follows and to instill a better appreciation of the inventor's contribution to the art. Before any embodiment of the invention is explained in detail, however, it must be made clear that the following details of construction, descriptions of geometry, and illustrations of inventive concepts are mere examples of the many possible manifestations of the invention.

DETAILED DESCRIPTION

As is the case with many inventions, the present invention for a phallus retention harness is subject to a wide variety of embodiments. However, to ensure that one skilled in the art will fully understand and, in appropriate cases, be able to practice the present invention, certain preferred embodiments of the broader invention revealed herein are described below and shown in the accompanying drawing figures.

Figure 1:
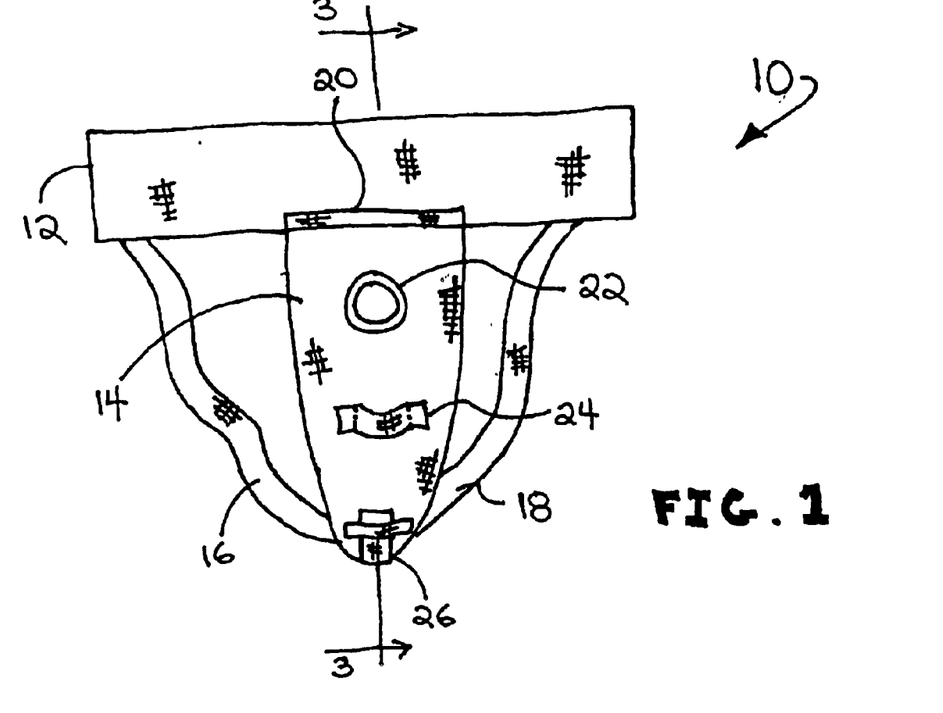
FIG. 1 is a view in front elevation of a phallus retention harness according to the present invention.
Figure 2:
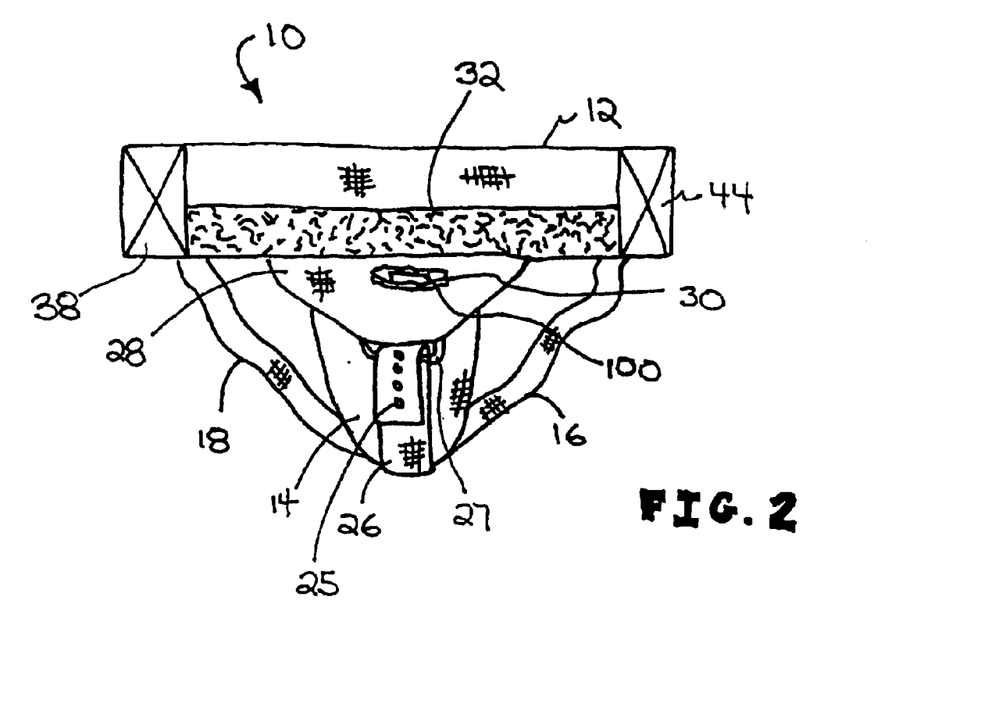
FIG. 2 is a view in rear elevation of the phallus retention harness of FIG. 1.
Figure 3:
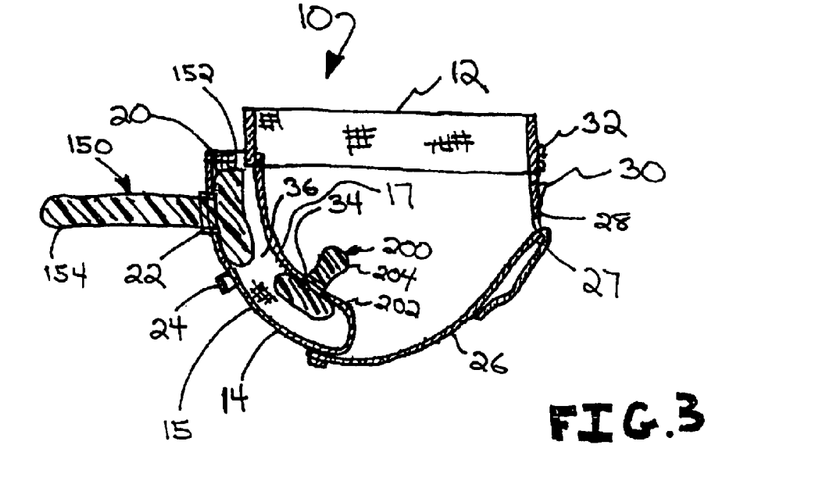
FIG. 3 is a cross-sectional view of the phallus retention harness taken along the line 3—3 in FIG. 1.

Looking more particularly to the drawings, a first preferred embodiment of the present invention for a phallus retention harness is indicated generally at 10 in FIGS. 1–3. In those drawings, the phallus retention harness 10 can be considered a crotch-type harness in that it is designed to retain a phallus, shown at 150 in FIG. 3, proximal to the crotch of a user. In the front elevational view of FIG. 1, one sees that the phallus retention harness 10 is founded on a pocket member 14 that receives and retains a proximal base portion 152 of a penile prosthetic or phallus 150. In this embodiment, as FIG. 3 shows, the pocket member 14 has an inner or rear panel 15 and an outer or front panel 17 and is formed of a soft and washable material so that it can be retained comfortably relative to a wearer's body.

The pocket member 14 in preferred embodiments can be formed by joined layers of resiliently stretchable material, which will preferably comprise a synthetic fabric. Suitable synthetic fabrics include LYCRA (a synthetic fiber produced by E. I. DuPont de Nemours and Company, Wilmington, Del.), DARLEXX (an elastic fabric produced by Darlington Fabrics Corporation, New York, N.Y.), NEOPRENE, and any other appropriate material or blend thereof. The front and rear panels 17 of the pocket member 14 each could be formed of a single layer, indeed a single piece, of material. In preferred embodiments, however, most advantageous function and support for a phallus 150 has been achieved by forming the front panel 15 with two layers of resiliently stretchable material of a given thickness to form an outside surface of the front panel 15 and two layers of resiliently stretchable material of a thicker thickness to form an inside surface of the front panel 15. In such a case, the rear panel 17 can be formed of two layers of resiliently stretchable material.

An upper end of the pocket member 14 is fixed, as by sewing or any other appropriate means, to a belt 12. A lower end of the pocket member 14 is secured, as by sewing or any other appropriate means, to a proximal end of a thong/cinching strap 26. A distal end of the thong/cinching strap 26 can be adjustably coupled to a back portion 28. In turn, the back portion 28 is fixed to a rear portion of the belt 12. Advantageously, the back portion 28 forms a small pocket 30 that can be used to retain, for example, a condom 100. As FIG. 2 shows most clearly, the thong/cinching strap 26 incorporates a means for adjusting the effective length of the thong/cinching strap 26 and thus the effective size of the phallus retention harness 10. In this case, that adjusting means comprises grommets 25 in combination with a belt-type latching mechanism 27.

As FIG. 2 shows, the thong/cinching strap 26 can be supplemented or replaced by first and second leg straps 16 and 18. In this embodiment, each of the first and second leg straps 16 and 18 has a proximal end fixed, as by sewing or by any other suitable means, to the lower end of the pocket member 14. A distal end of each leg strap 16 and 18 is fixed to a rear portion of the belt 12.

Under this arrangement, where the leg straps 16 and 18 are included, a user can put the harness 10 on by passing his or her legs through the leg straps 16 and 18 and sliding the harness 10 into position adjacent to his or her crotch. Where the thong/cinching strap 26 is additionally or alternatively included, the user can put the harness 10 into a wearing position by sliding the belt 12 into an appropriate and comfortable position about his or her waist and then securing the thong/cinching strap 26 in place. With this, the harness 10 will be retained snugly but comfortably in place.

Advantageously, the fit of the harness 10 can be adjusted further by a means for adjusting the circumference of the belt 12. Of course, the adjusting means could assume a wide variety of embodiments. Under this exemplary embodiment, the adjusting means comprises hook or loop material 32 disposed on the back of the belt 12 in combination with first and second adjustment tabs 38 and 44 that have loop or hook material 32 disposed thereon. With this, the harness 10 can be readily adjusted to accommodate wearers of different girths by adjusting the position of one or both adjustment tabs 38 and/or 44 relative to the rear portion of the belt 12.

Looking again to FIG. 1, one sees that a primary aperture 22 is disposed in the outer wall of the pocket member 14 for allowing the phallus 150 to pass therethrough. The periphery of the primary aperture 22 advantageously is resiliently expandable to accommodate phalluses 150 of varying diameters and configurations. FIG. 1 also shows that a hold down or restraining strap 24 is fixed, as by sewing or any other appropriate means, to the outer surface of the front panel 15 of the pocket member 14. In this embodiment, the hold down strap 24 is disposed in alignment below the primary aperture 22. Preferably, the hold down strap 24 is formed from a resiliently stretchable material. As its name would suggest, the hold down strap 24 can be used to hold down the elongate body portion 154 of the phallus 150. This can be useful where a wearer seeks to wear the harness 10 under his or her clothing or where a wearer seeks to simulate the appearance or feel of a flaccid penis.

Under this arrangement, a phallus 150, such as the one shown in FIG. 3, can be received and retained by the harness 10 such that it can be worn comfortably by the user. The phallus 150 shown in FIG. 3 has a base portion 152 and an elongate body portion 154. Typically, such a phallus 150 is formed, such as by molding or the like, of a single piece of material such as soft rubber. The pocket member 14 has an open top 20. With that, to insert the phallus 150 into the pocket member 14, the user need only insert the elongate body portion 154 of the phallus 150 into the open inner volume 36 of the pocket member 14 through the open top 20 and then push the elongate portion through the primary aperture 22 until the base portion 152 of the phallus 150 contacts the inner surface of the front panel 15 of the pocket member 14.

Figure 14:
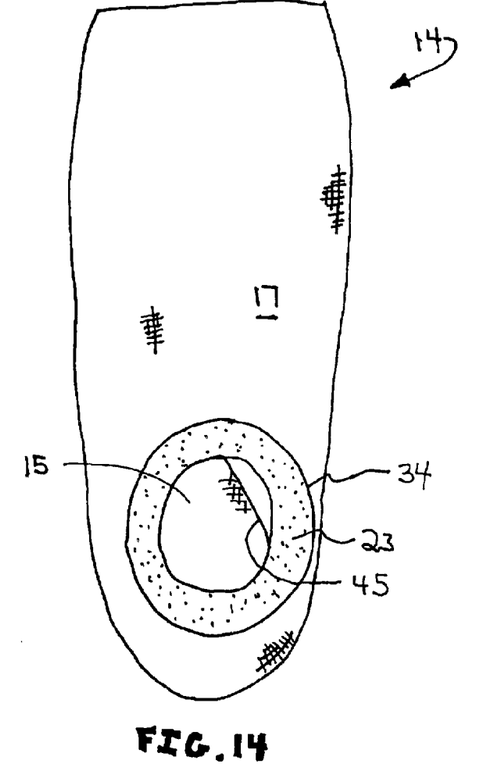
FIG. 14 is a view in front elevation of an alternative pocket member.

As FIGS. 3 and 14 further show, the pocket member 14 can have a secondary aperture 34 disposed in its inner panel 17. The secondary aperture 34 can be used for receiving and retaining a second phallus 200 that projects inwardly from the pocket member 14. When so disposed, the second phallus 200 can contact or be received into the genitalia of the wearer. As is shown in FIG. 3, the second phallus 200 has a base portion 202 that is fixed to a projecting portion 204. The projecting portion 204 in this exemplary embodiment is in plug form. A flap 45 can be provided in the outer panel 15 of the pocket member 14 in alignment with the secondary aperture 34 for enabling easy insertion and removal of the second phallus 200 relative to the secondary aperture 34. Furthermore, as FIG. 14 shows, a flat elastic ring 23 can be secured at the periphery of the secondary aperture 34 for securely retaining the second phallus 200.

Figure 4:
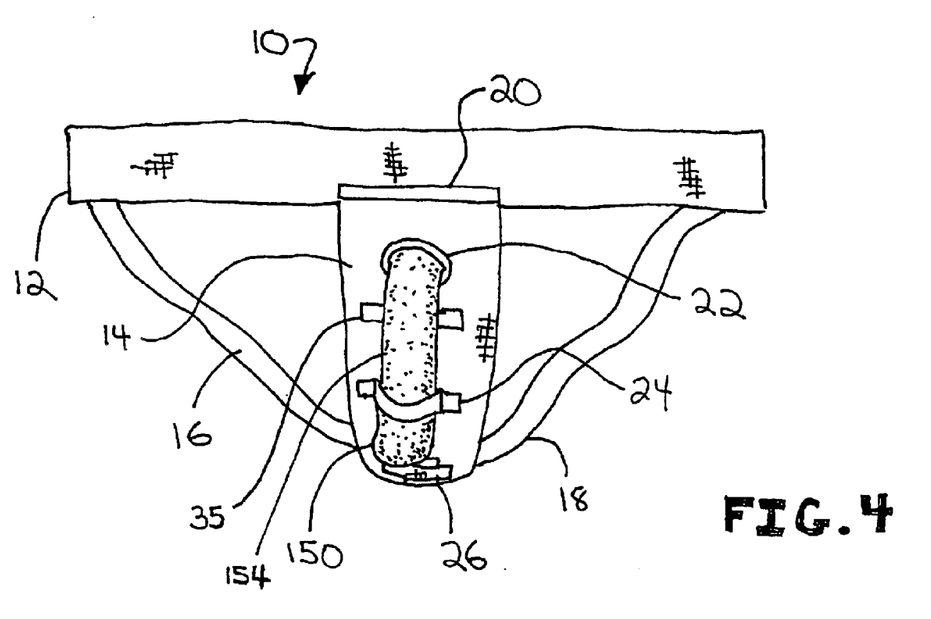
FIG. 4 is a view in front elevation of a phallus retention harness retaining a phallus.

In FIG. 4, the phallus retention harness 10 is shown in front elevation retaining a phallus 150 with a base portion 152 of the phallus 150 disposed in the pocket member 14 and the elongate body portion 154 of the phallus 150 extending therefrom. As it might be when the phallus 150 and the phallus retention harness 10 are to be worn under the clothing of a user, the elongate body portion 154 of the phallus 150 is shown as being restrained adjacent to the pocket member 14 by the hold down strap 24. Notably, although it is not being employed in FIG. 4, the phallus retention harness 10 in this embodiment further includes a supplementary hold down strap 35 for holding down a mid-portion of the phallus 10 if necessary or desirable.

Of course, the dimensions of the pocket member 14 could vary widely within the scope of the present invention. In this preferred embodiment, the aperture 22 has a diameter of approximately 1 and ½ inches. The upper edge of the aperture 22 is preferably disposed about 1 and ½ inches from the top of the pocket member 14. The hold down strap 24 can have a bowed, free central portion of about 1 and ½ inches across for receiving the phallus 150 and secured end portions of about ¾ inches across.

Figure 15:
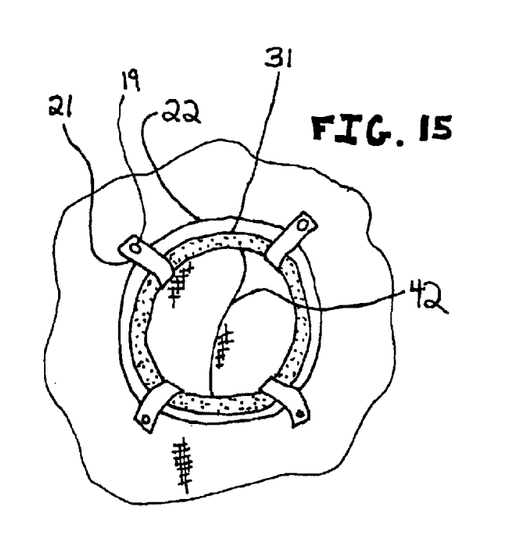
FIG. 15 is a view in front elevation of an alternative aperture construction.

FIG. 15 shows an alternative construction of the aperture 22. There, the aperture 22 is lined with a ring 31 for enhancing sexual activity. The ring 31 is removably and replacably retained by a plurality of straps 21. Each strap 21 has a first end fixed within the aperture 22 and a second end with a snap 19 for fixing the strap 21 and the ring 31 in place. The ring 31 and strap 21 combination can be particularly useful where a user is a male who passes his own penis (not shown) through the aperture 22 through the flap 42, which will be discussed more fully below.

Figure 5:
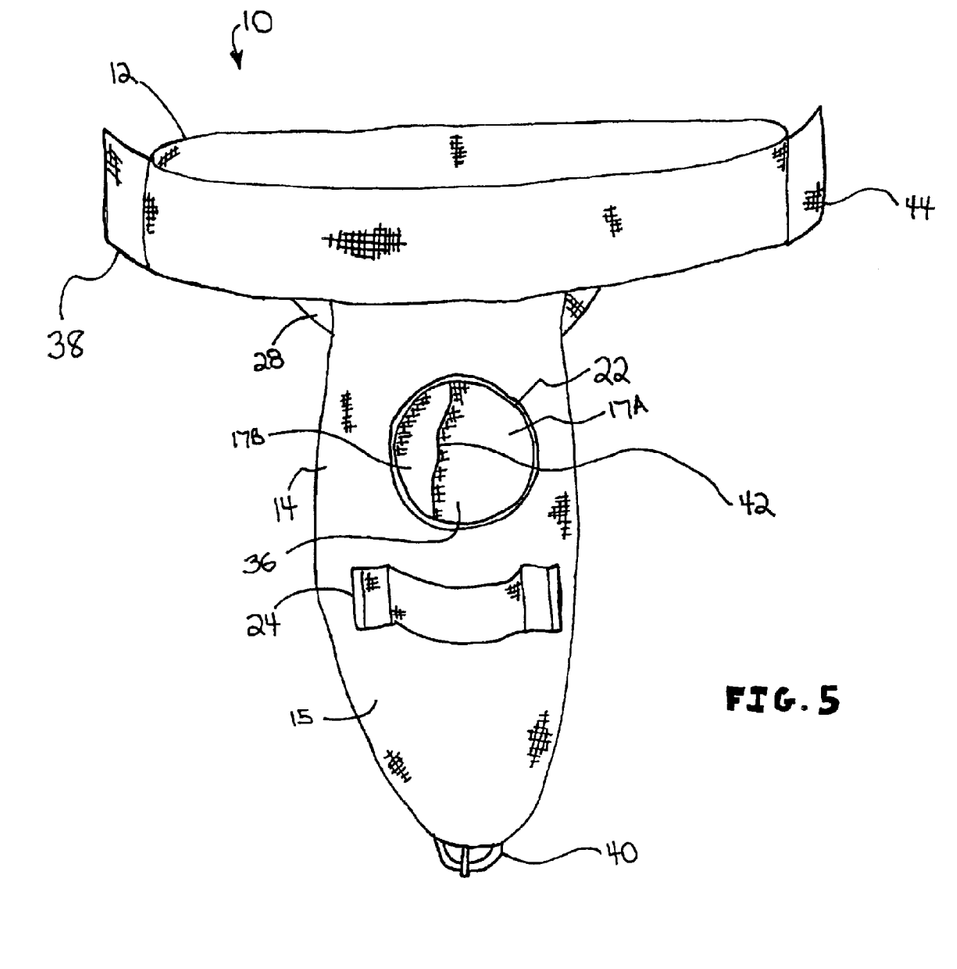
FIG. 5 is a view in front elevation of an alternative embodiment of the phallus retention harness.
Figure 6:
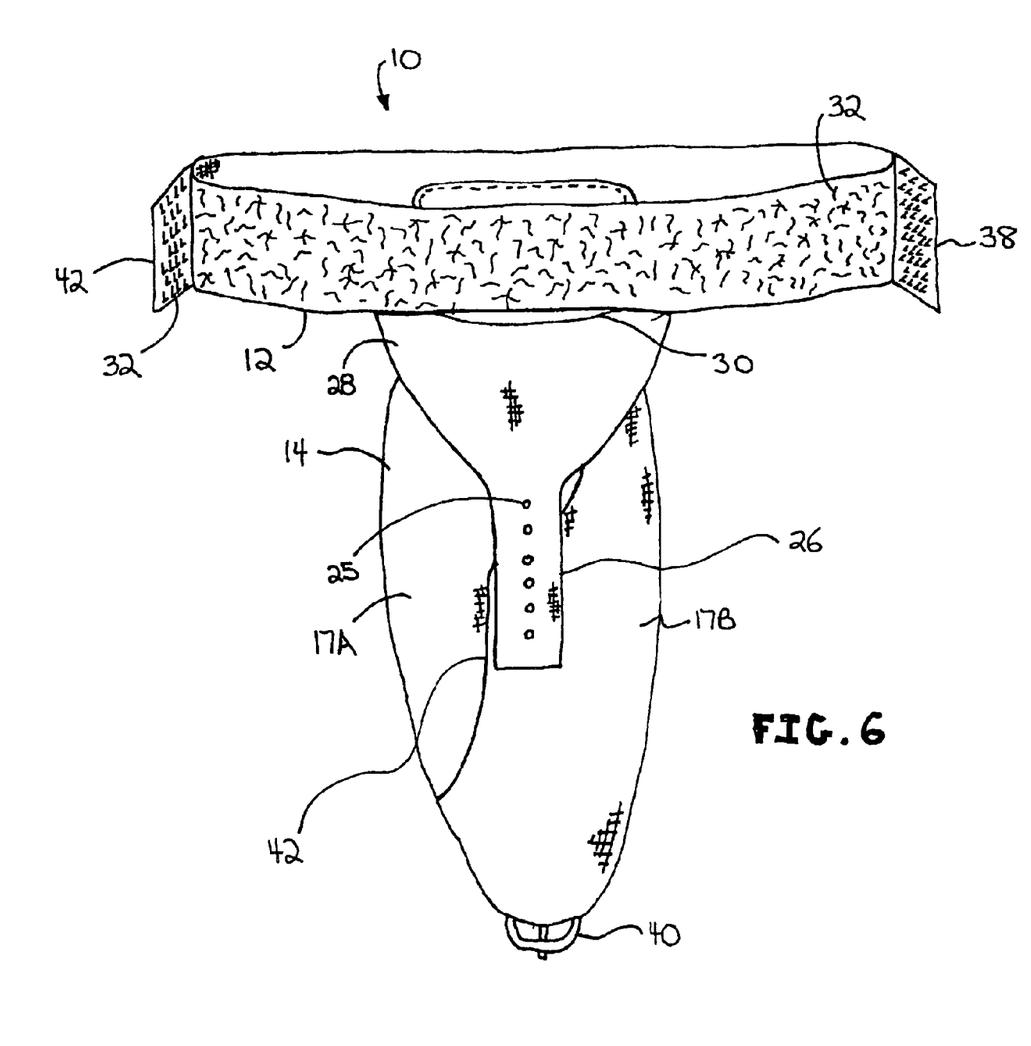
FIG. 6 is a view in rear elevation of the phallus retention harness of FIG. 5.

Turning to FIGS. 5 and 6, one sees an alternative embodiment of the crotch-type phallus retention harness 10. There, the phallus retention harness 10 again is founded on a pocket member 14 with an upper end coupled to a front portion of a belt 12. The belt 12 includes a length of hook or loop material 32 disposed along the outer surface of its entire back portion, and first and second adjustment tabs 38 and 44 extend from the belt 12 and have loop or hook material 32 disposed on their inner surfaces. With this, the effective circumference of the belt 12 can be readily adjusted.

A back portion 28, which again incorporates a pocket 30 for retaining condoms and other items, is again coupled to a rear portion of the belt 12. In this embodiment, a thong/cinching strap 26 extends from the back portion 28 and has a plurality of apertures 25 disposed therealong. A latching mechanism 40 is fixed to a lower end of the pocket member 14 for engaging and retaining the thong/cinching strap 26 via the plurality of apertures 25 whereby the effective size of the phallus retention harness can be further adjusted. A hold down strap 24 is again provided for restraining a phallus.

This embodiment departs from the previously described embodiments in that it does not include the first and second leg straps 16 and 18. Furthermore, the upper end of the pocket member 14 is not open for allowing an insertion of a phallus into the pocket member 14. Instead, the insertion of the phallus is enabled by a formation of the rear panel of the pocket member 14 as first and second flap panels 17A and 17B that overlap to create a flap 42. Under this arrangement, access to the open inner volume 36 of the pocket member 14 can be readily obtained by peeling back the first and/or second flap panels 17A and/or 17B to create an opening as is shown relative to an alternative embodiment in FIG. 8.

With the first and/or second flap panels 17A and/or 17B so peeled back, the elongate body portion 154 of the phallus 150 can be readily passed through the aperture 22 until the base portion 152 of the phallus 150 is fully disposed in the open inner volume 36. With that, the first and/or second flap panels 17A and/or 17B can be closed, and the phallus retention harness 10 can be used and worn. If necessary or desirable, hook and loop material (not shown) can be used to retain the first and second panels 17A and 17B in a closed configuration.

Figure 7:
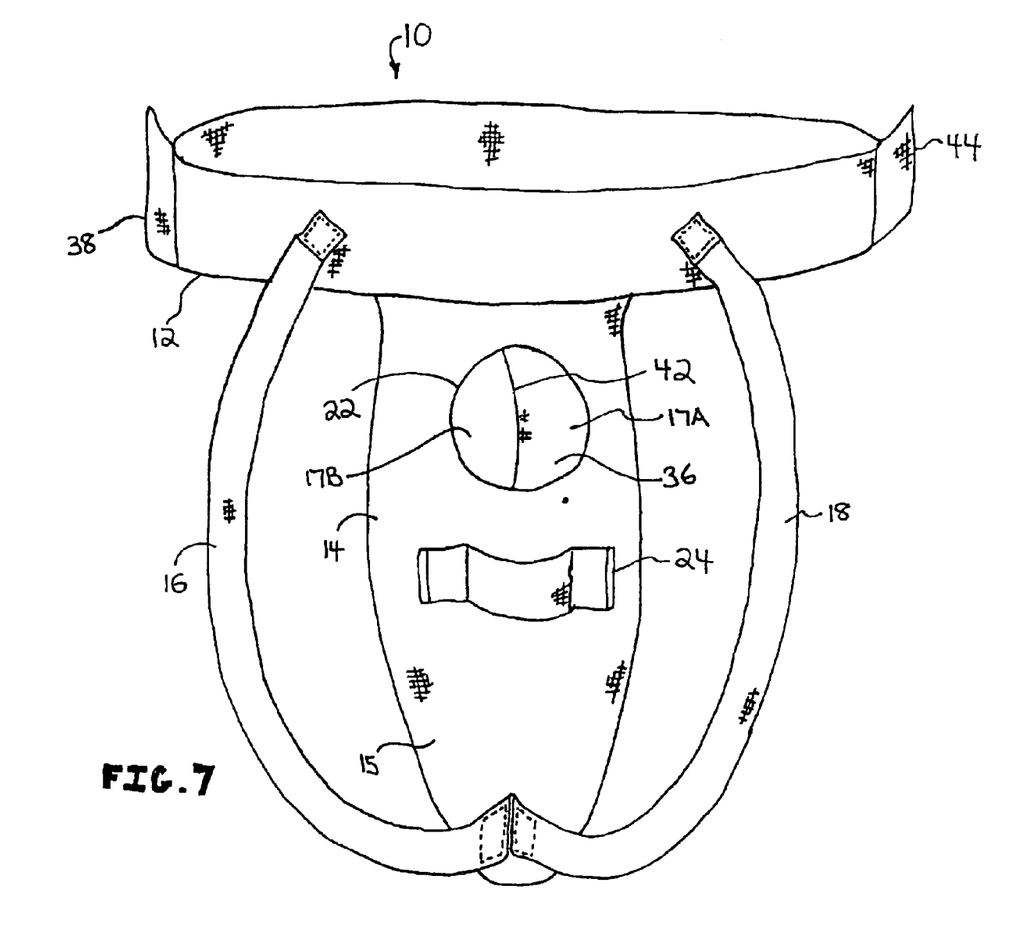
FIG. 7 is a view in front elevation of another embodiment of the phallus retention harness.
Figure 8:
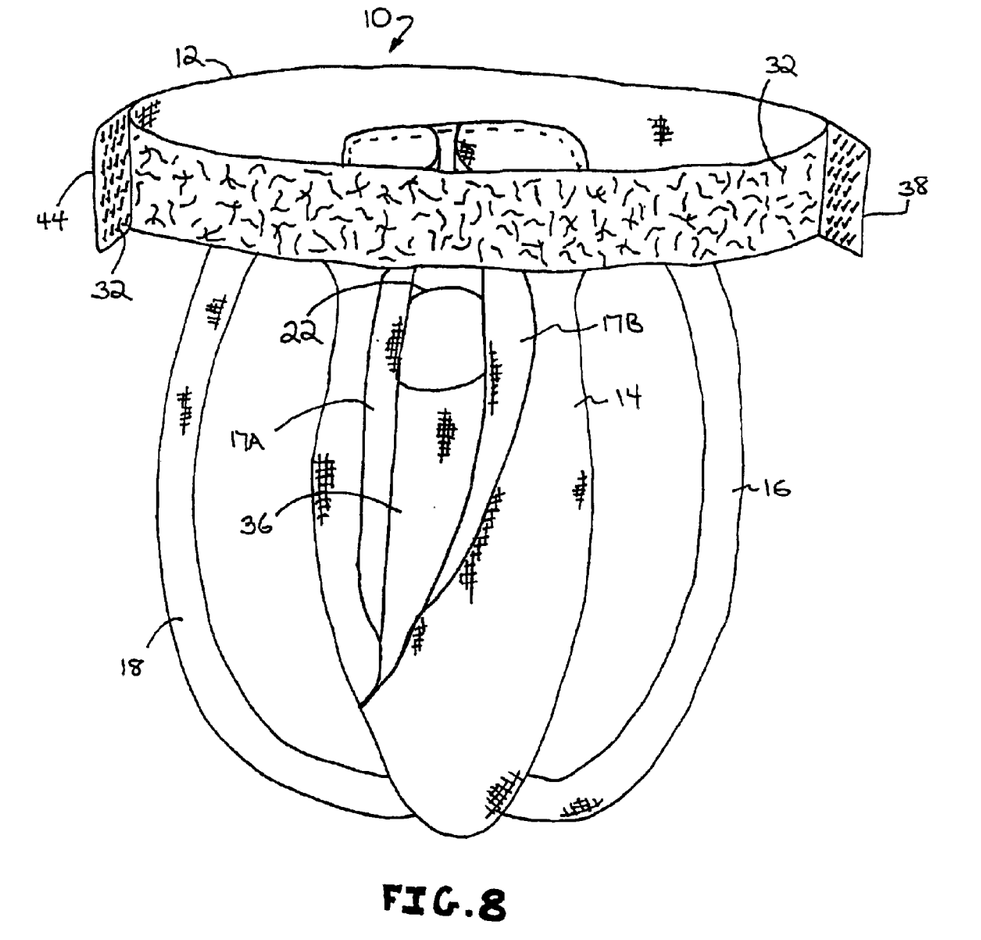
FIG. 8 is a view in rear elevation of the phallus retention harness of FIG. 7.

FIGS. 7 and 8 show another embodiment of the phallus retention harness 10 that is again designed to retain a phallus 150 adjacent to a users crotch. This embodiment eliminates the back portion 28 and the thong/cinching strap 26 and instead incorporates first and second leg straps 16 and 18. Each of the first and second leg straps 16 and 18 has an upper end fixed to the front, outer surface of the belt 12 and a lower end fixed to the lower, outer surface of the front panel 15 of the pocket member 14. Preferably, the leg straps 16 and 18 are elasticized. As FIG. 8 shows, the first and second flap panels 17A and 17B can be opened to allow access to the open inner volume 36 of the pocket member 14 and the aperture 22 in the front panel 15 thereof thereby allowing a ready insertion and removal of a phallus 150.

Figure 9:
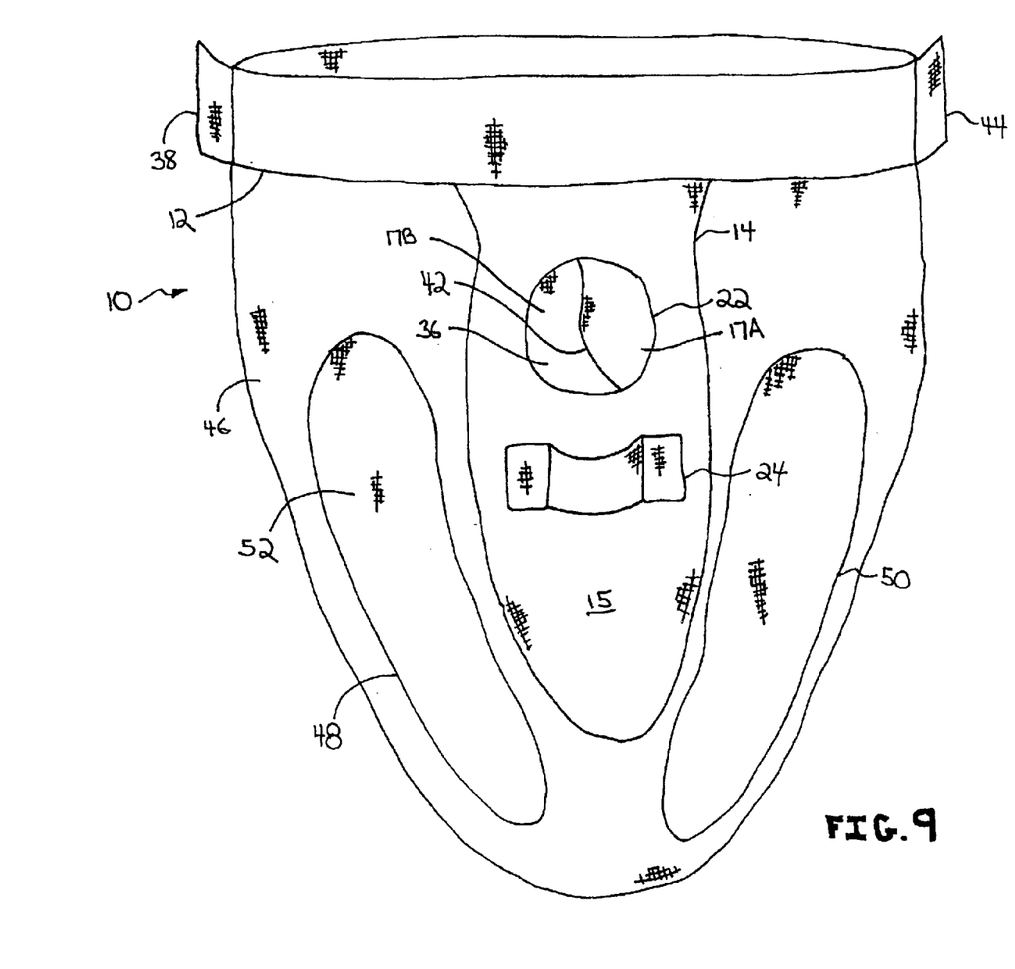
FIG. 9 is a view in front elevation of yet another embodiment of the phallus retention harness.

FIG. 9 shows still another crotch-type phallus retention harness 10. In this embodiment, however, the phallus retention harness 10 takes the form of a pair of underwear briefs. The phallus retention harness 10 again has a belt 12 with first and second adjustment tabs 38 and 44 for allowing an adjustment of the circumference of the belt 12. However, the leg straps 16 and 18 and the back portion 28 and thong/cinching strap 26 are foregone in favor of a body-fitting brief member 46 with first and second leg openings 48 and 50. The pocket member 14 is centrally disposed on the brief member 46, again incorporating an outer panel 15 and first and second inner flap panels 17A and 17B for enabling access to the open inner volume 36 of the pocket member 14. A hold down strap 24 again enables a user to restrain a phallus 150 that is being retained by the pocket member 14.

Figure 10:
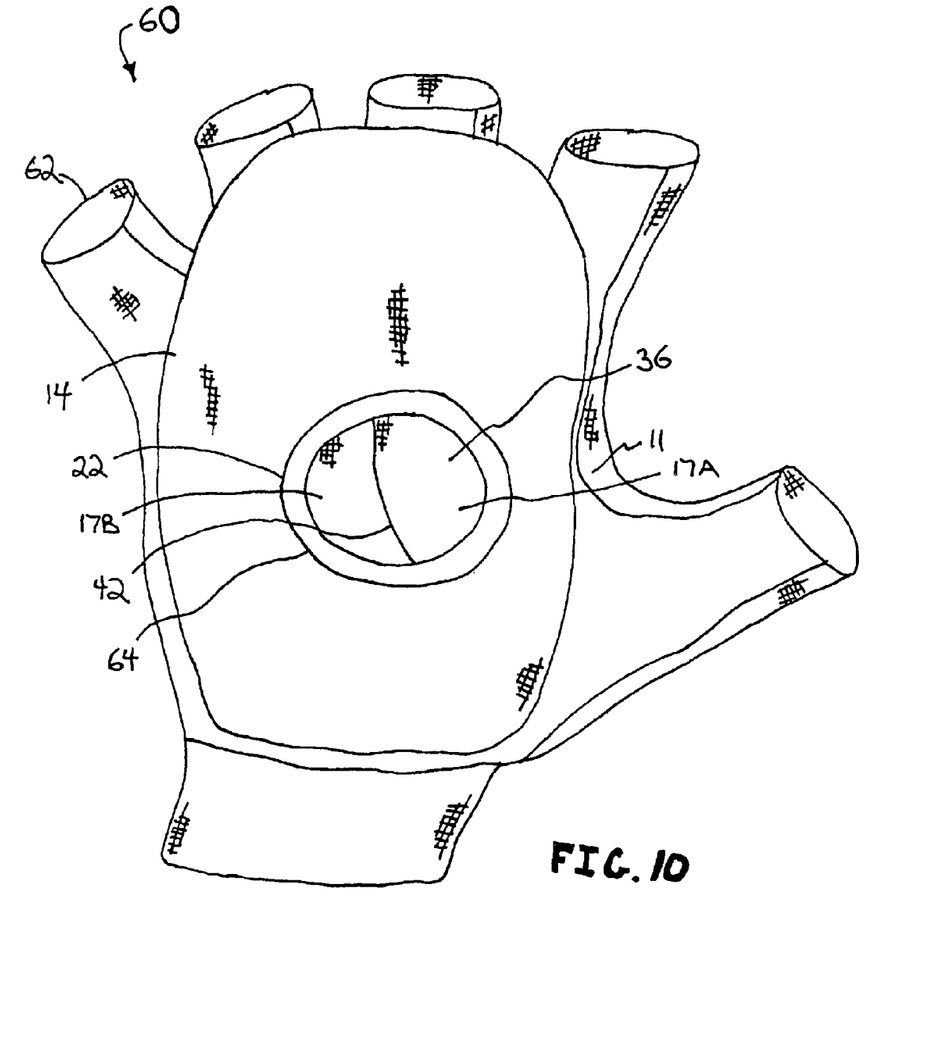
FIG. 10 is a bottom plan view of an embodiment of the phallus retention harness in the form of a glove.
Figure 11:
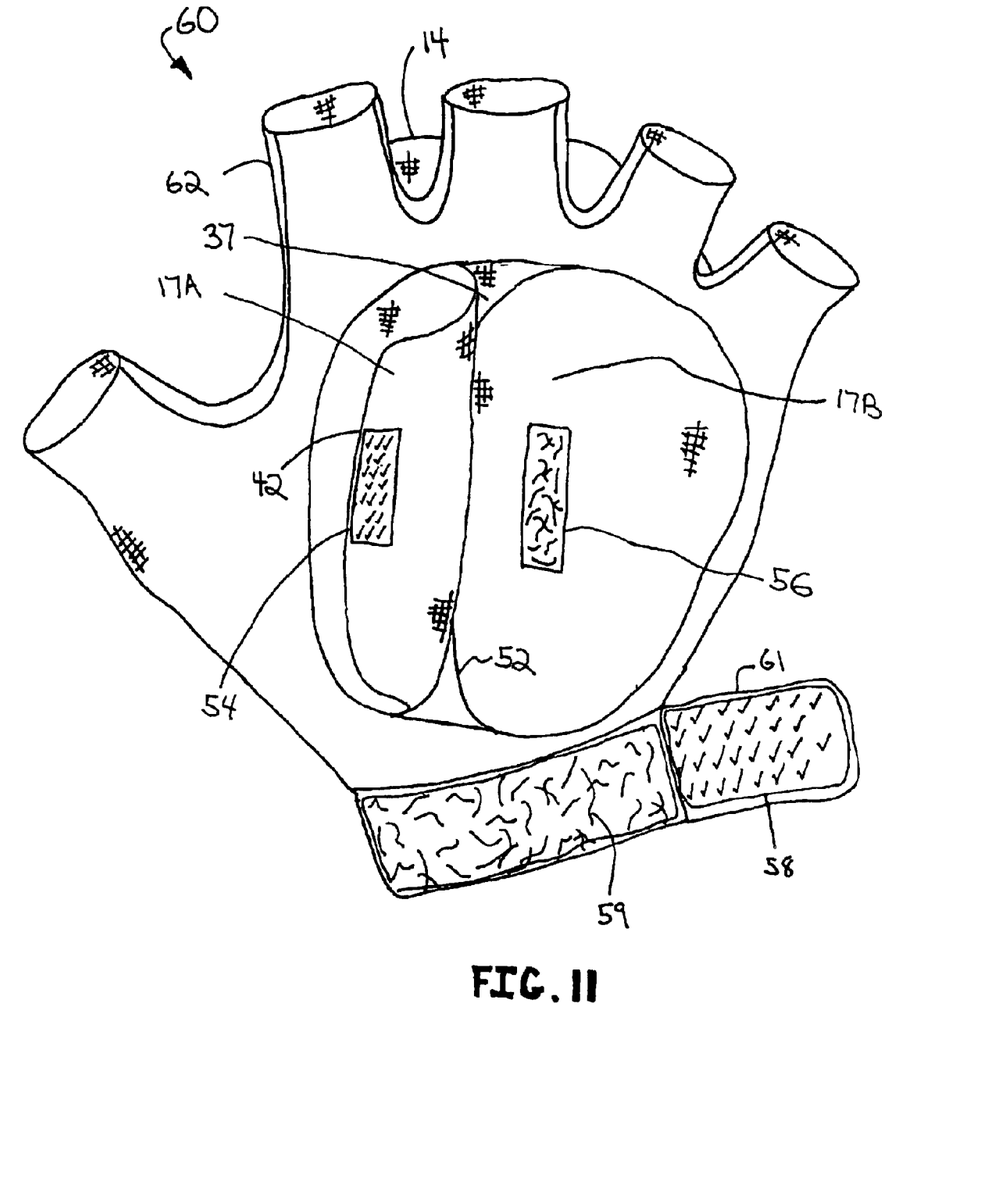
FIG. 11 is a top plan view of the glove-type phallus retention harness of FIG. 10.

FIGS. 10 and 11 shows a further embodiment of the phallus retention harness in the form of a glove, which is indicated generally at 60, to act as a hand-retained arrangement. As such, the phallus retention harness 60 has a body portion 11 with a plurality of truncated fingers 62. A pocket member 14 essentially forms a palm portion of the phallus retention harness 60. The pocket member 14 has an aperture 22 therein for enabling an elongate body portion 154 of a phallus 150 to pass therethrough. First and second flap panels 17A and 17B, shown most clearly in FIG. 11, allow access to the open inner volume 36 of the pocket member 14. A strip of hook material 54 is disposed on the first flap panel 17A while a strip of loop material 56 is disposed on the second flap panel 17B for enabling the first and second flap panels 17A and 17B to be retained in a closed configuration. Similarly, a strip of hook material 58 can be disposed on a flap 61 and a strip of loop material 59 can be disposed on a wrist portion of the phallus retention harness 60 for enabling the wrist size of the phallus retention harness 60 to be adjusted.

The phallus retention harness 60 could have an inner set of flap panels 17A and 17B for closing only the pocket member 14 and an outer set of flap panels 17A and 17B for closing the back portion of the glove-type phallus retention harness 60 in general. Under that arrangement, the open inner volume 36 of the pocket member 14 is separated from the main open inner volume 37 of the phallus retention harness 60 with the base portion 152 of the phallus 150 retained entirely in the open inner volume 36 and the user's hand retained in the main open inner volume 37. Alternatively, the phallus retention harness 60 could simply have an outer set of flap panels 17A and 17B whereby the user's hand and the base portion 152 of the phallus 150 would share the same open inner volume 36.

Figure 12:
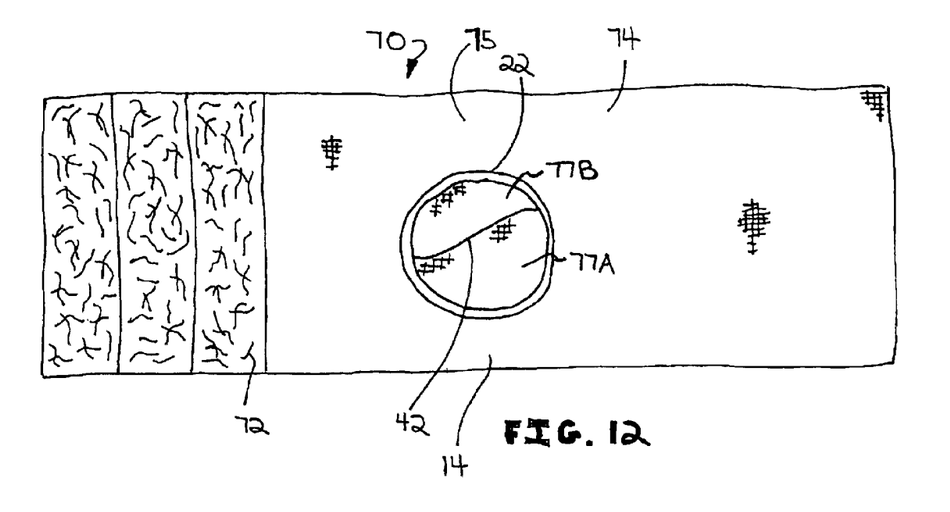
FIG. 12 is a top plan view of an embodiment of the phallus retention harness in the form of a strap.
Figure 13:
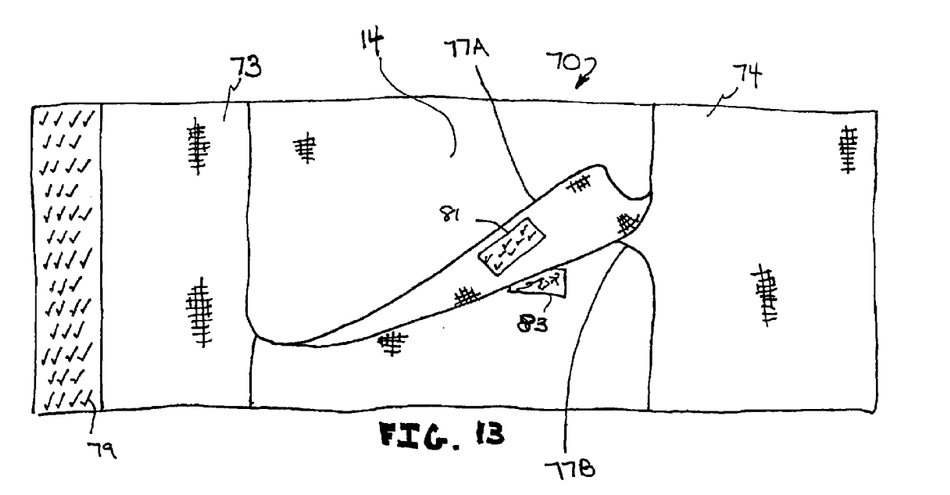
FIG. 13 is a bottom plan view of the strap-type phallus retention harness of FIG. 12.

FIGS. 12 and 13 depict still another embodiment of the phallus retention harness, this time in the form of a strap for surrounding a body part of a wearer, which is indicated at 70. The phallus retention harness 70 has an elongate body portion 74 of a given length and width. One or more strips 72, in this case three strips 72, of loop or hook material are disposed adjacent to a first end of the elongate body portion 74 on what may be considered a top panel 75 of the phallus retention harness 10. As FIG. 13 shows, a strip 79 of hook or loop material is disposed adjacent to a second end of the elongate body portion 74 on what may be considered the bottom panel 73 of the phallus retention harness 70. A portion of the top panel 75 helps form a pocket 14 that is centrally disposed along the elongate body portion 74, and an aperture 24 is provided in the pocket 14. First and second flap panels 77A and 77B cooperate to form a flap 42. When the first and second flap panels 77A and 77B are peeled back, access to the aperture 22 is provided from the bottom side of the phallus retention harness 70 to allow a user to insert the elongate body portion 154 of a phallus 150 therethrough until the base portion 152 of the phallus 150 is fully received beyond the first and second flap panels 77A and 77B. Hook and loop strips 81 and 83 are provided on the first and second flap panels 77A and 77B for retaining them in a closed configuration.

The phallus retention harness 70 and its components could, of course, be formed with substantially any dimensions and of substantially any suitable material. In this exemplary embodiment, the elongate body portion 74 has a phallus retention harness 70 has an overall length of roughly 21 and ½ inches and an overall width of approximately 5 and ½ inches. The three strips 72 of loop or hook material span substantially the entire width of the phallus retention harness 70 and themselves have a width of 2 inches thereby presenting a total length along the phallus retention harness 70 of 6 inches. The preferred aperture 22 has a diameter of approximately 1 and ½ inches and has a center longitudinally centered on the elongate body portion 74 and disposed approximately 8 and ¾ inches from the first end of the elongate body portion 74. Under such an arrangement, with a phallus 150 fully retained therein, the phallus retention harness 70 can be disposed surrounding a wearer's body part, such as the wearers thigh, and employed as the user so desires.

From the foregoing, it will be clear that the present invention has been shown and described with reference to certain preferred embodiments that merely exemplify the broader invention revealed herein. Certainly, those skilled in the art could conceive of alternative embodiments. For instance, those with the major features of the invention in mind could craft embodiments that incorporate those major features while not incorporating all of the features included in the preferred embodiments. Therefore, the following claims are intended to define the scope of protection to be afforded the inventors. Those claims shall be deemed to include equivalent constructions insofar as they do not depart from the spirit and scope of the invention.

It must be further noted that a plurality of the following claims may express certain elements as means for performing a specific function, at times without the recital of structure or material. As the law demands, these claims shall be construed to cover not only the corresponding structure and material expressly described in this specification but also equivalents thereof.

I claim as deserving the protection of Letters Patent:

1. A phallus retention harness for retaining a phallus with a base portion and an elongate body portion relative to a wearer, the phallus retention harness comprising:

a pocket member for receiving and retaining the phallus wherein the pocket member has a first panel and a second panel with an inner volume between the front panel and the rear panel;

an aperture in the front panel of the pocket member for enabling the elongate body portion of the phallus to extend therethrough whereby the phallus can be retained by the phallus retention harness with the base portion of the phallus disposed within the inner volume and the elongate body portion of the phallus projecting through the aperture; and a means for retaining the pocket member relative to the wearer's body.

2. The phallus retention harness of claim 1 wherein the means for retaining the pocket member relative to the wearer's body comprises a belt with a front portion and a rear portion for being disposed about a wearer's waist wherein an upper portion of the pocket member is coupled to the front portion of the belt and a means for retaining a lower portion of the pocket member adjacent to the wearer's crotch.

3. The phallus retention harness of claim 2 wherein the means for retaining the lower portion of the pocket member adjacent to the wearer's crotch comprises first and second leg straps.

4. The phallus retention harness of claim 2 wherein the means for retaining the lower portion of the pocket member adjacent to the wearer's crotch comprises a cinching strap with a first end for coupling with the lower portion of the pocket member and a second end for coupling with the rear portion of the belt.

5. The phallus retention harness of claim 4 further comprising a back portion fixed to the rear portion of the belt wherein the second end of the cinching strap is coupled to the back portion.

6. The phallus retention harness of claim 5 further comprising a pocket disposed in the back portion for retaining articles.

7. The phallus retention harness of claim 1 wherein the phallus retention harness further comprises a hold down strap fixed to the first panel of the pocket member for restraining the elongate body portion of the phallus.

8. The phallus retention harness of claim 7 wherein the phallus retention harness further comprises a second hold down strap fixed to the front panel of the pocket member for supplementing the hold down strap in restraining the elongate body portion of the phallus.

9. The phallus retention harness of claim 1 wherein the phallus retention harness further comprises a secondary aperture in the second panel of the pocket member whereby a second phallus can be retained by the phallus retention harness with a body portion extending from the pocket member generally oppositely to the phallus that projects from the aperture.

10. The phallus retention harness of claim 9 wherein the phallus retention harness further comprises a flat ring of resilient material fixed about a periphery of the secondary aperture.

11. The phallus retention harness of claim 1 wherein the phallus retention harness further comprises a ring for being associated with the aperture and means for retaining the ring relative to the aperture.

12. The phallus retention harness of claim 2 wherein the phallus retention harness further comprises a means for adjusting the circumference of the belt comprising hook or loop material disposed on an outside surface of the belt, an adjustment tab coupled to the belt, and loop or hook material disposed on an inside surface of the adjustment tab for engaging the hook or loop material disposed on the belt.

13. The phallus retention harness of claim 1 wherein the first panel and the second panel are formed from flexible material.

14. The phallus retention harness of claim 13 wherein the first panel and the second panel are formed from resiliently stretchable material and wherein the aperture is resiliently expandable to accommodate phalluses of varying diameters and configurations.

15. The phallus retention harness of claim 14 wherein the first panel is formed from two layers of resiliently stretchable material of a given thickness to form an outside surface of the first panel and two layers of resiliently stretchable material of a thicker thickness to form an inside surface of the first panel and wherein the second panel is formed of two layers of resiliently stretchable material.

16. The phallus retention harness of claim 1 further comprising a means for enabling an insertion of the phallus into the inner volume of the pocket member to allow the elongate body portion of the phallus to be inserted through the aperture from within the inner volume.

17. The phallus retention harness of claim 16 wherein the means for enabling an insertion of the phallus into the inner volume of the pocket member comprises an open end of the pocket member.

18. The phallus retention harness of claim 17 wherein the means for enabling an insertion of the phallus into the inner volume of the pocket member comprises a flap disposed in the second panel generally opposite to the aperture.

19. The phallus retention harness of claim 18 wherein the flap is formed by first and second flap panels that overlap to create the flap whereby ready access to the aperture can be provided by a peeling back of the first and second flap panels.

20. The phallus retention harness of claim 19 wherein the phallus retention harness further comprises a hook and loop combination disposed on the first and second panels for retaining the first and second panels in a closed configuration.

21. The phallus retention harness of claim 1 wherein the means for retaining the pocket member relative to the wearer's body comprises an underwear brief arrangement.

22. The phallus retention harness of claim 1 wherein the means for retaining the pocket member relative to the wearer's body comprises a glove body portion with a plurality of fingers for being disposed on a wearer's hand.

23. The phallus retention harness of claim 1 wherein the means for retaining the pocket member relative to the wearer's body comprises a strap elongate body portion for surrounding a body part of a wearer.

* * * * *